(12) United States Patent
Molenaar et al.

(10) Patent No.: US 7,067,288 B2
(45) Date of Patent: Jun. 27, 2006

(54) NUCLEOTIDE SEQUENCES WHICH CODE FOR THE MDHA GENE

(75) Inventors: Douwe Molenaar, Baesweiler (NL); Michel Eduard Van Der Rest, Venlo (NL); Andre Drysch, Toenisvorst (DE)

(73) Assignee: Degussa AG, Duesseldorf (DE)

( * ) Notice: Subject to any disclaimer, the term of this patent is extended or adjusted under 35 U.S.C. 154(b) by 51 days.

(21) Appl. No.: 10/727,516

(22) Filed: Dec. 5, 2003

(65) Prior Publication Data

US 2004/0142454 A1 Jul. 22, 2004

Related U.S. Application Data

(62) Division of application No. 09/892,867, filed on Jun. 28, 2001, now Pat. No. 6,995,002.

(30) Foreign Application Priority Data

Jul. 4, 2000 (DE) ................. 100 32 350

(51) Int. Cl.
*C12P 13/04* (2006.01)
*C12N 9/10* (2006.01)
*C12N 1/20* (2006.01)
*C12N 15/00* (2006.01)
*C07H 21/04* (2006.01)

(52) U.S. Cl. .............. 435/106; 435/115; 435/183; 435/193; 435/252.3; 435/252.32; 435/320.1; 536/23.2

(58) Field of Classification Search ............... 435/106, 435/115, 183, 189, 252.3, 252.32, 320.1, 435/193; 536/23.2
See application file for complete search history.

(56) References Cited

FOREIGN PATENT DOCUMENTS

| | | |
|---|---|---|
| EP | 1 108 790 | 6/2001 |
| WO | WO 99/18228 | 4/1999 |
| WO | WO 01/00802 | 1/2001 |
| WO | WO 01/00804 | 1/2001 |
| WO | WO 01/00844 | 1/2001 |

OTHER PUBLICATIONS

Bernard J. Eikmanns, et al., Antonie Van Leeuwenhoek, vol. 46 pp. 145-163, "Molecular Aspects of Lysine, Threonine, and Isoleucine Biosynthesis in Corynebacterium Glutamicum," 1993.

Douwe Molenaar, et al., Journal of Bacteriology, vol. 182, No. 24, pp. 6884-6891, "Functions of the Membrane-Associated and Cytoplasmic Malate Dehydrogenases in the Cirtric Acid Cycle of Corynebacterium Glutamicum," Dec. 2000.

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

The invention provides nucleotide sequences from coryneform bacteria which code for maltate dehydrogenase and a process for the fermentative preparation of amino acids using bacteria in which the mdhA gene is attenuated.

26 Claims, 1 Drawing Sheet

NUCLEOTIDE SEQUENCES WHICH CODE FOR THE MDHA GENE

CROSS-REFERENCE TO RELATED APPLICATION

The present application claims priority to German Application No. DE 10032 350.2 filed Jul. 4, 2000, the entire contents of which are incorporated herein by reference.

BACKGROUND OF THE INVENTION

1. Field of the Invention

The invention provides nucleotide sequences from coryneform bacteria which code for malate dehydrogenase and a process for the fermentive preparation of amino acids using bacteria in which the mdhA gene is attenuated.

2. Discussion of the Background

L-Amino acids, in particular lysine, are used in human medicine, in pharmaceuticals, in foodstuffs and in animal nutrition.

It is known that amino acids are prepared by fermentation from strains of Coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acids.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of the mdhA gene encoding a malate dehydrogenase would improve L-amino acid yields. Thus, the present inventors had the object of providing new methods for improved fermentative preparation of amino acids, in particular L-lysine.

SUMMARY OF THE INVENTION

One object of the present invention, is providing a new process adjuvant for improving the fermentative production of L-amino acids, particularly L-lysine and L-glutamate. Such process adjuvants include attenuated bacteria, preferably attenuated Coryneform bacteria which express attenuated levels of the malate dehydrogenase which is encoded by the mdhA gene.

Thus, another object of the present invention is providing such a bacterium, which expresses attenuated amounts of the malate dehydrogenase or gene products of the mdhA gene. Another object of the present invention is providing a bacterium, preferably a Coryneform bacterium, which expresses a polypeptide that has an attenuated malate dehydrogenase activity.

Another object of the invention is to provide a nucleotide sequence encoding a polypeptide which has a malate dehydrogenase sequence. One embodiment of such a sequence is the nucleotide sequence of SEQ ID NO: 2.

A further object of the invention is a method of making a malate dehydrogenase or an isolated polypeptide having malate dehydrogenase activity, as well as use of such isolated polypeptides in the production of amino acids. One embodiment of such a polypeptide is the polypeptide having the amino acid sequence of SEQ ID NO: 3. In one embodiment, the isolated polypeptide comprises at its N terminus the amino acid sequence of SEQ ID NO:1.

Other objects of the invention include methods of detecting nucleic acid sequences homologous to SEQ ID NO: 2, particularly nucleic acid sequences encoding polypeptides that have the activity of malate dehydrogenase, and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is especially preferred.

L-Amino acids, in particular lysine, are used in human medicine and in the pharmaceuticals industry, in the foodstuffs industry and very particularly in animal nutrition. There is therefore a general interest in providing new improved processes for the preparation of amino acids, in particular L-lysine.

The invention provides an isolated polynucleotide from Coryneform bacteria, comprising a polynucleotide sequence which codes for the mdhA gene, chosen from the group consisting of a) polynucleotide which is identical to the extent of at least 70% to a polynucleotide which codes for a polypeptide which comprises the amino acid sequence of SEQ ID No. 3,
b) polynucleotide which codes for a polypeptide which comprises an amino acid sequence which is identical to the extent of at least 70% to the amino acid sequence of SEQ ID No. 3,
c) polynucleotide which is complementary to the polynucleotides of a) or b), and
d) polynucleotide comprising at least 15 successive nucleotides of the polynucleotide sequence of a), b), or c), the polypeptide preferably having the activity of malate dehydrogenase.

The invention also provides an isolated polypeptide with malate dehydrogenase activity, which comprises the amino acid sequence according to SEQ ID No. 1.

The invention also provides the polynucleotide according to claim 1, this preferably being a DNA which is capable of replication, comprising:

(i) the nucleotide sequence shown in SEQ ID no. 2, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides:

a DNA which is capable of replication and comprises the nucleotide sequence as shown in SEQ ID No. 2,
a vector containing the polynucleotide as claimed in claim 1, point d, in particular pEMmdhAint, deposited in *E. coli* DSM 13494 on 18.05.2000 at the DSMZ [German Collection of Microorganisms and Cell Cultures], Braunschweig (Germany),
and Coryneform bacteria which contain a deletion or insertion in the mdhA gene, in particular using the vector pEMmdhAint.

The invention also provides polynucleotides which substantially comprise a polynucleotide sequence, which are obtainable by screening by means of hybridization of a corresponding gene library, which comprises the complete mdhA gene with the polynucleotide sequence corresponding to SEQ ID No. 2, with a probe which comprises the sequence of the polynucleotide mentioned, according to SEQ ID no. 2 or a fragment thereof, and isolation of the DNA sequence mentioned.

Polynucleotide sequences according to the invention are suitable as hybridization probes for RNA, cDNA and DNA, in order to isolate, in the full length, nucleic acids, or polynucleotides or genes which code for malate dehydrogenase or to isolate those nucleic acids or polynucleotides or genes which have a high similarity of sequence with that of the malate dehydrogenase gene.

Polynucleotide sequences according to the invention are furthermore suitable as primers with the aid of which DNA of genes which code for malate dehydrogenase can be prepared with the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds.

The polypeptides according to the invention include the polypeptides according to SEQ ID No. 3, in particular those with the biological activity of malate dehydrogenase, and also those which are at least 70%, preferably at least 80% and in particular at least 90% to 95% identical to the polypeptide according to SEQ ID No. 3 and have the activity mentioned.

The invention moreover provides a process for the fermentative preparation of amino acids, in particular lysine, using Coryneform bacteria which in particular already produce the amino acids, and in which the nucleotide sequences which code for the mdhA gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene, or allele, which codes for a corresponding enzyme with a low activity, or inactivates the corresponding gene or enzyme (protein), and optionally combining these measures.

The microorganisms which the present invention provides can prepare amino acids, in particular lysine, from glucose, sucrose, lactose, fructose, maltose, molasses, starch, cellulose or from glycerol and ethanol. They can be representatives of Coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum,* are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants, or strains, prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM5714 and
*Corynebacterium glutamicum* DSM12866.

Preferably, a bacterial strain with attenuated expression of a mdhA gene that encodes a polypeptide with activity of malate dehydrogenase will improve amino acid yield at least 1%.

The inventors have succeeded in isolating the new mdha gene of C. glutamicum which codes for the enzyme malate dehydrogenase (EC 1.1.1.37).

For this, the malate dehydrogenase enzyme protein is first purified to homogeneity by chromatographic methods. Methods and instructions for protein purification and preparation are described e.g. in the textbook by Schleifer and Wensink: Practical Methods in Molecular Biology (Springer Verlag, Berlin, Germany, 1981); in the handbook by Harris and Angal: Protein Purification Methods: A Practical Approach (IRL Press, Oxford, UK, 1989); in the textbook by Scopes: Protein Purification: Principles and Practice, $3^{rd}$ ed. (Springer Verlag, New York, USA, 1993), and in generally known textbooks and handbooks. The pure enzyme protein can then be broken down into peptides by treatment with suitable enzymes, such as, for example, trypsin or chymotrypsin. The amino acid sequence of these peptides can be determined by the method of N-terminal sequencing described by Edman (Archives of Biochemistry 22, 475 (1949)). It is likewise possible to determine the N-terminal amino acids of the purified enzyme protein directly. Methods and instructions for protein sequencing are described, for example, in Smith: Protein Sequencing Protocolls [sic]: Methods in Molecular Biology, Vol. 64 and Vol. 112 (Humana Press, Totowa, N.J., USA, 1996) and in Kamp et al.: Protein Structure Analysis: Preparation, Characterization, and Microsequencing (Springer Verlag. New York, N.Y., USA, 1997). In this manner the amino acid sequence of the malate dehydrogenase enzyme protein can be determined in part or in full, depending on the outlay. The 20 N-terminal amino acids of the malate dehydrogenase enzyme protein isolated are shown in SEQ ID No. 1.

Utilizing the known use of codons for Coryneform bacteria (Malumbres et al. (Gene 134, 15–24 (1993)), synthetic oligonucleotides can be synthesized and can be employed as primers for amplification of the corresponding chromosomal DNA segments by means of the polymerase chain reaction (PCR). Instructions for this are to found by the expert, inter alia, for example in the handbook by Gait: Oligonukleotide [sic] synthesis: a practical approach (IRL Press, Oxford, UK, 1984) and in Newton and Graham: PCR (Spektrum Akademischer Verlag, Heidelberg, Germany, 1994). The DNA fragment of the sod gene obtained in this manner is then cloned by known methods, as described e. g. in Sambrook et al.: Molecular Cloning: A Laboratory Manual $2^{nd}$ ed. (Cold Spring Harbor Laboratory Press, USA, 1989) and can be employed as a probe for the search for the complete gene, including its 5' and 3' flanks, in gene libraries.

It is likewise possible to isolate the complete gene, including its 5' and 3' flanks, by the method of "plasmid rescue". In this method, a fragment of the gene of interest, which has been obtained, for example, in the manner described above, is cloned in a plasmid vector which is not replicative for Coryneform bacteria. The plasmid vector containing the gene fragment is incorporated or integrated into the target gene of the host by transformation and subsequent homologous recombination. The target gene is thereby marked. The chromosomal DNA of the strain marked in this way is then isolated and digested with a suitable restriction enzyme. Suitable restriction enzymes are, in particular, those which do not cleave within the vector DNA employed. The resulting DNA fragments are circularized by treatment with ligase and a host suitable for replication of the plasmid vector, typically Escherichia coli, is transformed with the ligation mixture. Plasmid DNA is isolated from the transformants and the cloned DNA sections are sequenced. The method of "plasmid rescue" is described, for example, by Niaudet et al. (Gene 19, 277–284 (1982)). Methods of DNA sequencing are described, inter alia, by Sanger et al. (Proceedings of the National Academy of Sciences of the United States of America, 74:5463–5467, 1977) or in the protocol of Zimmerman et al. (BioTechniques 17:302 (1994)).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of C. glutamicum which codes for the mdhA gene and which, as SEQ ID No. 2, is a constituent of the present invention has been found in this manner. The amino acid sequence of the corresponding translation product or gene product has moreover been derived from the present DNA sequence by the methods described above. The resulting amino acid sequence of the mdhA gene product is shown in SEQ ID No. 3. It is known (O'Regan et al., Gene 77, 237–251 (1989)), that the amino acid methionine or formyl-methionine coded by the start codon ATG is removed from various proteins by enzymes of the host.

Coding DNA sequences which result from SEQ ID No. 2 by the degeneracy of the genetic code are also a constituent of the invention. In the same way, DNA sequences which hybridize with SEQ ID No. 2 or parts of SEQ ID No. 2 are a constituent of the invention. Finally, DNA sequences which are prepared by the polymerase chain reaction (PCR) using primers which result from SEQ ID No. 2 are a constituent of the invention.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found by the expert, inter alia, in the handbook by Gait: Oligonukleotide [sic] synthesis: a practical approach (IRL Press, Oxford, UK, 1984) and in Newton and Graham: PCR (Spektrum Akademischer Verlag, Heidelberg, Germany, 1994).

In the work on the present invention, it has been found that Coryneform bacteria produce amino acids, in particular L-lysine, in an improved manner after attenuation of the mdhA gene.

To achieve an attenuation, either the expression of the mdhA gene or the catalytic properties of the enzyme proteins can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e. g. in the patent application WO 96/15246, in Boyd and Murphy (Journal of Bacteriology 170: 5949 (1988)), in Voskuil and Chambliss (Nucleic Acids Research 26: 3548 (1998)), in Jensen and Hammer (Biotechnology and Bioengineering 58: 191 (1998)), in Patek et al.

(Microbiology 142: 1297 (1996)), Vasicova et al. (Journal of Bacteriology 181: 6188 (1999)) and in known textbooks of genetics and molecular biology, such as e. g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum:* Aufhebung der allosterischen Regulation und Struktur des Enzyms [Threonine dehydratase from *Corynebacterium glutamicum:* Cancelling the allosteric regulation and structure of the enzyme]", Reports from the Jülich Research Centre, Jül-2906, ISSN09442952, Jülich, Germany, 1994). Comprehensive descriptions can be found in known textbooks of genetics and molecular biology, such as e. g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e. g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

A common method of mutating genes of *C. glutamicum* is the method of gene disruption and gene replacement described by Schwarzer and Pühler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of *C. glutamicum*.

Figure 1:
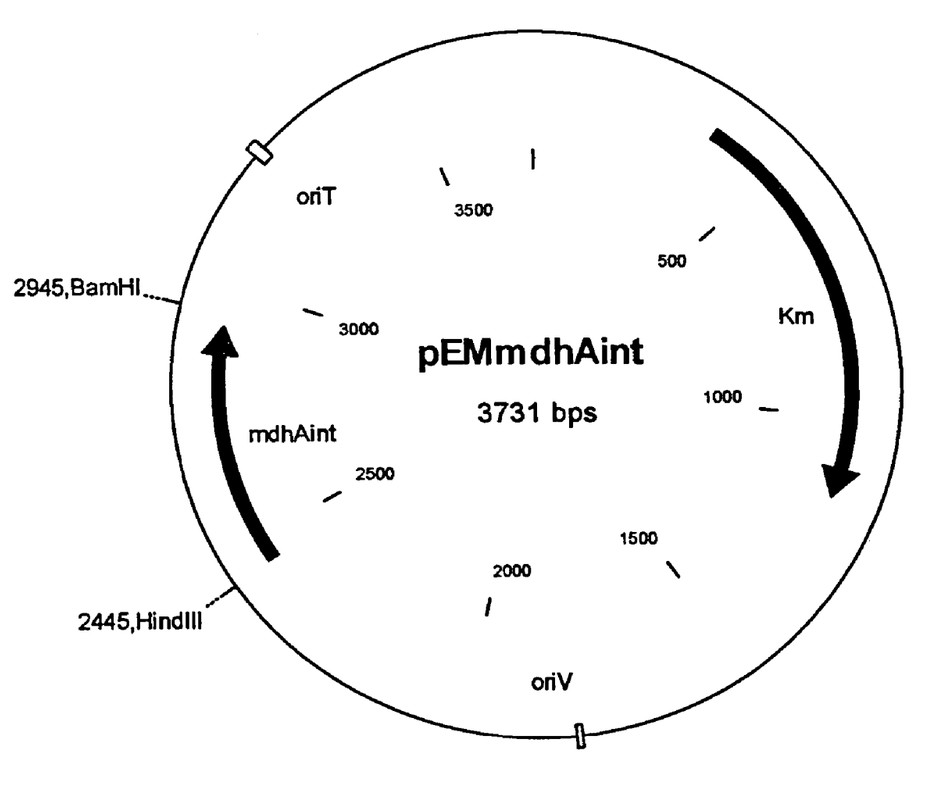
FIG. 1: Map of the plasmid pEMmdhAint.

FIG. 1 shows by way of example the plasmid vector pEMmdhAint, with the aid of which the mdha gene can be disrupted or eliminated.

In the method of gene replacement, a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch (Microbiology 144, 915–927 (1998)) to eliminate the pyc gene of *C. glutamicum* by a deletion.

A deletion, insertion or a base exchange can be incorporated into the mdhA gene in this manner.

In addition, it may be advantageous for the production of L-amino acids, in particular L-lysine, to enhance, in particular to over-express, one or more enzymes of the particular biosynthesis pathway, of glycolysis, of anaplerosis, of the pentose phosphate cycle or of amino acid export, in addition to attenuation of the mdhA gene.

Thus, for example, for the preparation of L-lysine, at the same time one or more of the genes chosen from the group consisting of the dapA gene which codes for dihydrodipicolinate synthase (EP-B 0 197 335), the eno gene which codes for enolase (DE: 19947791.4), the zwf gene which codes for the zwf gene product (JP-A-09224661), the pyc gene which codes for pyruvate carboxylase (Eikmanns (1992), Journal of Bacteriology 174:6076–6086), the lysE gene which codes for lysine export (DE-A-195 48 222)

can be enhanced, in particular over-expressed.

It may furthermore be advantageous for the production of amino acids, in particular L-lysine, in addition to the attenuation of the mdhA gene, at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase (U.S. Ser. No. 09/396,478, DSM 12969), the poxB gene which codes for pyruvate oxidase (DE: 1995 1975.7, DSM 13114)

to be attenuated.

In addition to attenuation of the mdha gene it may furthermore be advantageous, for the production of amino acids, in particular L-lysine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine. A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The following microorganism was deposited at the Deutsche Sammlung für Mikroorganismen und Zellkulturen (DSMZ=German Collection of Microorganisms and Cell Cultures, Braunschweig, Germany) in accordance with the Budapest Treaty on 18.05.2000:

*Escherichia coli* DH5αmcr/pEMmdhAint as DSM13494

The process according to the invention is used for the fermentative preparation of amino acids, in particular L-lysine.

Having generally described this invention, a further understanding can be obtained by reference to certain specific examples which are provided herein for purposes of illustration only, and are not intended to be limiting unless otherwise specified.

EXAMPLES

The isolation of plasmid DNA from *Escherichia coli* and all techniques of restriction, Klenow and alkaline phosphatase treatment were carried out by the method of Sambrook et al. (Molecular cloning. A Laboratory Manual (1989) Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

The malate dehydrogenase activity was determined as described by Sanwal (Journal of Biological Chemistry 244 (7):1831–1837 (1969)) and Smith (Methods of Enzymatical Analysis, 1985, ed. 3, volume 3 (Bergmeyer et al. (eds.)), VCH Verlagsgesellschaft, Weinheim, Germany). Protein concentrations were measured by the method of Smith et al. (Analytical Biochemistry 150:76–85 (1985)).

Example 1

Isolation and Purification of Malate Dehydrogenase from *Corynebacterium glutamicum* ATCC 13032

Four times, 100 ml 2×TY were inoculated with in each case a colony of the strain *Corynebacterium glutamicum* ATCC 13032 and in each case cultured in 250 ml conical flasks for 16 hours at 30° C. and 200 revolutions per minute. The cells were washed twice in buffer A (50 mM K phosphate, pH 7.5, 1 mM dithiothreitol, 2 mM ethylenediaminetetraacetic acid) at 4° C., and resuspended in 20 ml of the same buffer. The cells were broken down three times in a precooled French Pressure Cell from Spectronic Unicam (Rochester, N.Y., USA) under 165 MPa. The cell debris was then sedimented in a centrifuge at 4° C. for 10 minutes at 75600×g. The malate dehydrogenase protein was purified in three steps.

Step 1

Streptomycin Sulfate Precipitation:

The supernatant was removed and further treated with a streptomycin sulfate precipitation. For this, a 10 percent (weight/volume) streptomycin sulfate solution was slowly added, while stirring at 0° C., until a final concentration of 0.75% was reached. The batch was incubated for 15 minutes on ice and then centrifuged for 10 minutes at 4° C. and 15000×g. The supernatant was then introduced into a dialysis hose pretreated in accordance with the manufacturers instructions (Medicell, London, UK) and dialysed twice in each case in 1 l buffer B (10 mM K phosphate, pH 7.5, 1 mM dithiothreitol, 2 mM ethylenediaminetetraacetic acid) for 1.5 hours at 4° C. The dialysate was then centrifuged for 15 minutes at 4° C. and 75600×g.

Step 2

Anion Exchanger Chromatography:

The supernatant from step 1 was removed and introduced on to an anion exchanger column of the type "Resource Q" (1 ml column volume, Amersham Pharmacia, Freiburg, Germany) equilibrated with 4 column volumes of buffer B. The column was flushed with 4 column volumes of buffer B and then eluted with a linear gradient from buffer B to buffer C (10 mM K phosphate, pH 7.5, 1 mM dithiothreitol, 2 mM ethylenediaminetetraacetic acid, 1 M NaCl) in 15 column volumes. The anion exchanger chromatography was carried out at 20° C. and the fractions were collected at 4° C. The malate dehydrogenase was eluted at approx. 0.5 M NaCl. The fractions which contained malate dehydrogenase activity were combined and then desalinated by means of gel filtration over PD-10 columns (Amersham Pharmacia, Freiburg, Germany) with ice-cold buffer D (10 mM K phosphate, pH 7.5) in accordance with the manufacturer's instructions.

Step 3

Dyestuff Affinity Chromatography:

Less than 10 mg total protein from step 2 were introduced on to a column filled with 2.5 ml of the column material "Reactive Brown 10" (Sigma, Deisenhofen, Germany) and equilibrated with 12.5 ml buffer D. The column was flushed with 15 ml ice-cold buffer D and the malate dehydrogenase was eluted with 2.5 ml buffer E (10 mM K phosphate, pH 7.5. 1 mM NADH). The eluate was desalinated by means of gel filtration over PD-10 columns as described above.

Step 4

Dyestuff Affinity Chromatography:

Step 3 was repeated.

The protein purified in this way was stored at −20° C. For stabilization of the activity, the sample was supplemented with 1 mg/ml bovine serum albumin. The supplementation with bovine serum albumin was omitted in the case of samples employed for determination of the N-terminal sequence of the malate dehydrogenase protein. A Lambda-10 spectrophotometer from Perkin Elmer (Foster City, Calif. USA) was used for measuring the activity of the purified enzyme. The purified malate dehydrogenase had a maximum specific oxalacetate-reducing activity of 1200 to 1300 µmol/min and mg protein at a concentration of 0.1 mM oxalacetate and 0.3 mM NADH.

The purity of the malate dehydrogenase isolated was determined by means of SDS-polyacrylamide gel electrophoresis. The analysis showed that the purified malate dehydrogenase was present as a homogeneous protein with an apparent molecular weight of 33 kDa.

Example 2

Determination of the N-Position Amino Acid Sequence

The N-position amino acid sequence of the purified malate dehydrogenase protein was determined by Edman degradation (Edman, Molecular Biology Biochemistry Biophysics 8:211–55(1970)) by means of the automatic sequencer model 476A from PE Biosystems (Foster City, Calif., USA). The resulting amino acid sequence (see also SEQ ID No. 1) was:

Asn-Ser-Pro-Gln-Asn-Val-Ser-Thr-Lys-Lys-Val-Thr-Val-Thr-Gly-Ala-Ala-Gly-Gln-Ile.

Example 3

Preparation of a Vector with a Copy of an Internal Fragment of the mdha Gene

A segment of the mdhA gene was amplified by means of the polymerase chain reaction (PCR) starting from chromsomal [sic] DNA of the strain ATCC13032 and then cloned.

With the aid of the N-position amino acid sequence determined in example 2, the degenerated primer P1 was discarded. This primer had the sequence:
5'-AARGTYACYGTYACYGGY-3' (SEQ ID NO:4).

The primers [sic] P2, which had the following sequence, was employed as the second degenerated primer:
5'-CGRTTRTGRTCVARRCG-3' (SEQ ID NO:5).

The abbreviation R stands for the nucleobases A or G, the abbreviation Y stands for C or T and the abbreviation V stands for A, G or C.

The primers shown were synthesized by MWG Biotech (Ebersberg, Germany). The PCR reaction was carried out by the standard PCR method of Innis et al., (PCR protocols. A guide to methods and applications, 1990, Academic Press, New York, USA). Genomic DNA of *Corynebacterium glutamicum* ATCC13032, which was isolated by the method described by Pospiech and Neumann (Trends in Genetics 11:217–218 (1995)), was used as the template.

In the polymerase chain reaction, a cycle comprising denaturing (30 seconds, 94° C.), annealing (60 seconds, 63° C.) and synthesis (90 seconds, 72° C.) was passed through 30 times. A last synthesis of 10 minutes at 72° C. was then carried out. The Taq polymerase from Promega (Madison, Wis., USA) and a Thermocycler from Techne (Cambridge, UK) were used.

The DNA fragment of the mdhA gene approx. 470 bp long prepared in this manner was purified with the aid of the QIAQuick PCR Purification Kit from Qiagen (Hilden, Germany) and cloned into the EcoRV cleavage site of the vector pBlueskript II SK(+) (Stratagene, La Jolla, Calif., USA). The fragment was then isolated with the aid of the restriction enzymes BamHI and HindIII and cloned into the vector pEM1 treated with the restriction enzymes BamHI and HindIII (Schrumpf et al. Journal of Bacteriology 173, 4510–4516 (1991)) in *E. coli* DHα, selection taking place on LB medium supplemented with 50 µg/ml kanamycin. The plasmid formed in this way was called pEMmdhAint.

Example 4

Determination of the Sequence of the mdhA Gene

In the strain *Corynebacterium glutamicum* ATCC 13032, the mdhA gene was inactivated with the aid of the plasmid pEMmdhAint.

The strain *Corynebacterium glutamicum* ATCC 13032 was transformed with the plasmid pEMmdhAint as described by Van der Rest et al (Applied Microbiology and Biotechnology 52,541–545 (1999)). Selection of the transformants was carried out on LBHIS agar, which had been supplemented with 25 mg/l kanamycin. LBHIS agar comprises LB medium, which has been supplemented with 18.5 g/l brain-heart broth (Becton Dickinson, Sparks Md., USA), 91 g/l sorbitol and 15 g/l agar-agar. The strain ATCC13032mdhA::pEMmdhAint, in which the plasmid pEMmdhAint is integrated in the mdha gene, was formed in this manner.

Chromosomal DNA was isolated from the strain ATCC13032mdhA::pEMmdhAint, as described by Pospiech and Neumann (Trends in Genetics 11:217–218 (1995)), and digested completely in two different batches, once with the restriction enzyme StuI and once with the restriction enzyme XbaI. The chromosomal restriction fragments were ligated as described by Niaudet et al. (Gene 19, 277–284 (1982)) and *Escherichia coli* DH5α-MCR (Grant et al Proceedings of the National Academy of Sciences U.S.A. 87,4645–4649 (1990)) was transformed with the ligation batch. Transformants were selected on LB agar with 50 mg/l kanamycin. Plasmid DNA was isolated from the transformants and subjected to a restriction analysis. The plasmids pEMmdhAint-StuI and pEMmdhAint-XbaI, which, in addition to the internal fragment of the mdhA gene 470 bp long already cloned in the plasmid pEMmdhAint, carried regions of the 5' and of the 3' end of the gene, were identified in this manner. The plasmid pEMmdhAint-StuI, obtained from the StuI digestion, additionally had 0.56 kb on the 5' end and 0.40 kb on the 3' end of the 470 bp region. The plasmid pEMmdhAint-XbaI, obtained from the XbaI digestion, additionally had 1.2 kb on the 3' end of the 470 bp region.

The plasmids obtained were sequenced by Seqlab (Göttingen, Germany) using the Cycle-Sequencing protocol of Zimmerman et al. (BioTechniques 17:302 (1994)). The sequences were evaluated with PC/Gene Version 6.60 from Intelligenetics Inc. (Geneva, Switzerland). The sequence of the mdha gene cluster is shown in SEQ ID No. 2.

Example 5

Preparation of L-Lysine Producers with an Inactivated mdhA Gene

Experiments were carried out with various known lysine producers of *C. glutamicum* in order to investigate the effect of elimination of the mdhA gene on the production of lysine.

1. Preparation of the Strains

The strain MH20-22B is described in EP-B-0435132 and is deposited as DSM5715 in accordance with the Budapest Treaty. The strain DM58-1 is described in EP-B-0358940. The transformant DM58-1pDM6 described there is deposited as DSM4697 in accordance with the Budapest Treaty. The strain DM58-1 can be prepared from DSM4697 by curing methods, such as, for example, by the method of "plasmid curing" described by Schäfer et al. (Journal of Bacteriology, 176, 7309–7319 (1994)). The strain DG 52-5 is described in DE-C-3823451. The transformant DG 52-5/pZ1-asd described there is deposited as DSM4421 in accordance with the Budapest Treaty. The strain DG52-5 can also be prepared from DSM4421 by the method of "plasmid curing".

The strain *Corynebacterium glutamicum* MH20-22B was transformed with the plasmid pEMmdhAint as described by Van der Rest et al. (Applied Microbiology and Biotechnology 52,541–545 (1999)). Selection of the transformants was carried out on LBHIS agar, which had been supplemented with 25 mg/l kanamycin. The strain MH20-22BmdhA::pEMmdhAint was formed in this manner. Starting from the strains DG52-5 and DM58-1, in each case the strains DG52-5mdhA::pEMmdhAint and DM58-1mdhA::pEMmdhAint were formed in the same manner.

2. Determination of the Malate Dehydrogenase Activity

To confirm the success of the insertion mutagenesis, the malate dehydrogenase activity was measured in the strains MH20-22B, DM58-1 and DG52-5 and in the insertion mutants MH20-22BmdhA::pEMmdhAint, DG52-5mdhA::pEMmdhAint and DM58-1mdhA::pEMmdhAint. For this, in each case a colony of the strains was inoculated on to 50 ml 2×TY medium and incubated for 16 hours in a 250 ml conical flask at 30° C. and 200 revolutions per minute. The media for the strains MH20-22BmdhA::pEMmdhAint, DG52-5mdhA::pEMmdhAint and DM58-1mdhA::pEMmdhAint additionally received 25 µg/ml kanamycin here. The cultures were centrifuged off for 10 minutes at 10000×g, washed twice with 50 mM potassium phosphate pH 7.5 and then suspended in 5 ml of the same buffer. The cell suspensions were broken down with two passes through an ice-cold French Press Cell under 165 MPa. The samples were then centrifuged for 10 minutes at 75000×g and 4° C. The clear supernatant was used as the crude extract for the malate dehydrogenase activity measurements. The malate dehydrogenase was determined, using as the buffer 100 mM 3-amino-1-propanol (pH 9.2) with additionally 4.5 mM MgCl2 [sic] and 2.9 mM $NAD^+$. The test batch contained 1 ml of this buffer and 50 µl of the crude extract. The batch was first incubated for 30 minutes at 30° C. Thereafter, the malate dehydrogenase reaction was started by addition of 25 mM neutralized L-malate. The absorption was measured at a wavelength of 340 nm in a Lambda-10 spectrophotometer from PE Biosystems (Foster City, Calif., USA). Measurement with the complete reaction batch without L-malate served as a control of the specific $NAD^+$ reduction rate.

The starting strains MH20-22B, DM58-1 and DG52-5 had a specific malate dehydrogenase activity of 301, 380 and 354 nmol/min×mg protein respectively, while the mdhA insertion mutants showed no detectable malate dehydrogenase activity. The lower detection limit here for the activity was 2 nmol/min×mg protein.

Example 6

Preparation of L-Lysine

The strains described in example 5 were incubated in 2×TY medium, which had been supplemented with kanamycin (25 µg/ml) in the case of the insertion mutants, for 24 hours at 30° C. For culturing in a liquid medium, the medium CgIII (Keilhauer et al. 1993, Journal of Bacteriology 175: 5595–5603), which had additionally been supplemented with kanamycin (25 mg/l) for the insertion mutants, was used. For this, 10 ml medium contained in a 100 ml conical flask were inoculated with a colony of the strain and the culture was then used further as a pre-culture.

CGXII-glucose minimal medium (Keilhauer et al. Journal of Bacteriology 175, 5595–5603 (1993)) was used as the production and test medium. The medium contained no kanamycin. Culturing was carried out in 500 ml conical flasks equipped with a metal spiral with a diameter of 2 cm lying along the edge on the base. These flasks were filled with 60 ml CGXII-glucose minimal medium. The cultures were inoculated with the pre-culture such that the optical density at the start had a value of between 0.5 and 0.6. Culturing was carried out for 72 hours at 30° C. The flasks were shaken with a frequency of 140 revolutions per minute.

After incubation for 72 hours, the optical density of the culture and the lysine concentration in the production medium were determined.

The optical density (OD) was determined with a Lambda B spectrophotometer from Perkin-Elmer at a wavelength of 600 nm.

L-Lysine was determined by means of "High Performance Liquid Chromatography", a "Hypersil ODS 5µ" column (dimensions: 125×4 mm) from Chromatographie-Service, Langerwehe, Germany, being used. The separation was carried out by means of a linear gradient of mobile phases A: 0.1 mM sodium acetate, pH 7.5 and B: methanol (ratio A:B of 85:15 to 0:100). 5 minutes before application the amino acids were derivatized with ortho-phthalodialdehyde (OPA reagent, Pierce, Rockford Ill., USA). Detection was carried out by measuring the fluorescence with an excitation wavelength of 243 nm and an emission wavelength of 436 nm. The result of the experiment is shown in table 1.

TABLE 1

| Strain | Optical density | L-Lysine (mM) |
| --- | --- | --- |
| MH20-22B | 37.1 | 26.1 |
| MH20-22BmdhA::pEMmdhAint | 36.5 | 29.3 |
| DG52-5 | 32.4 | 13.6 |
| DG52-5mdhA::pEMmdhAint | 48.7 | 44.4 |

TABLE 1-continued

| Strain | Optical density | L-Lysine (mM) |
| --- | --- | --- |
| DM58-1 | 42.0 | 32.2 |
| DM58-1mdhA::pEMmdhAint | 38.7 | 42.2 |

The abbreviations and designations used have the following meaning. The base pair numbers stated are approximate values obtained in the context of reproducibility of measurements.

mdhAint Internal fragment of the mdhA gene, bases 566 to 1035 of Seq. ID.NO. 1
Km gene Km resistance gene (Tn5)
oriV *E. coli* replication origin
oriT Origin for transfer (mobilization) from plasmid RP4
BamHI: Cleavage site of the restriction enzyme BamHI
HindIII: cleavage site of the restriction enzyme HindIII

The invention claimed is:

1. An isolated coryneform bacterium, which has been modified to express a decreased amount of malate dehydrogenase or to express a malate dehydrogenase with decreased activity compared to the corresponding unmodified strain, wherein said malate dehydrogenase has at least 95% homology to SEQ ID NO: 3.

2. The isolated coryneform bacterium of claim 1, wherein the polynucleotide encoding said malate dehydrogenase has been eliminated.

3. The isolated coryneform bacterium of claim 1, wherein expression of the polynucleotide encoding said malate dehydrogenase has been attenuated.

4. The isolated coryneform bacterium of claim 1, wherein the expression of the polynucleotide encoding said malate dehydrogenase has been attenuated by modification of at least one operator, promoter, attenuator, ribosome binding site, or start codon, which is operably associated with said polynucleotide.

5. The isolated coryneform bacterium of claim 1, which expresses said malate dehydrogenase with decreased activity compared to the corresponding unmodified strain.

6. The isolated coryneform bacterium of claim 1, which is of the genus *Corynebacterium* or *Brevibacterium*.

7. The isolated coryneform bacterium of claim 1, which is selected from the group consisting of *Corynebacterium glutamicum*, *Corynebacterium acetoglutamicum*, *Corynebacterium acetoacidophilum*, *Corynebacterium melassecola*, *Corynebacterium thermoaminogenes*, *Brevibacterium flavum*, *Brevibacterium lactofermentum*, and *Brevibacterium divaricatum*.

8. The isolated coryneform bacterium of claim 1 which comprises pEMmdhAint.

9. A process for making an L-amino acid comprising:
a) culturing the bacterium of claim 1 in a medium suitable for the production of said L-amino acid by fermentation, and
b) recovering said L-amino acid from the culture medium or from the bacterial cells.

10. The process of claim 9, wherein said amino acid is L-lysine.

11. The process of claim 9, wherein said amino acid is L-glutamate.

12. The process of claim 9, wherein in said bacterium the expression of the polynucleotide encoding said malate dehydrogenase has been eliminated or attenuated.

13. The process of claim 9, wherein in said bacterium the expression of the polynucleotide encoding said malate dehydrogenase has been attenuated by modification of at least one, operator, promoter, attenuator, ribosome binding site, or start codon, which is operably associated with said polynucleotide encoding said malate dehydrogenase.

14. The process of claim 9, wherein said bacterium which expresses said malate dehydrogenase with decreased activity compared to the corresponding unmodified strain.

15. The process of claim 9, wherein said bacterium is at least one selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum*.

16. The process of claim 9, wherein said bacterium is *Corynebacterium glutamicum*.

17. The process of claim 9, wherein said bacterium further comprises at least one polynucleotide whose expression is enhanced compared to an unmodified starting strain selected from the group consisting of:
the dapA polynucleotide which codes for dihydrodipicolinate synthase,
the eno polynucleotide which codes for enolase,
the zwf polynucleotide which codes for glucose-6-phosphate dehydrogenase,
the pyc polynucleotide which codes for pyruvate carboxylase, and
the lysE polynucleotide which codes for lysine exporter.

18. The process of claim 9, wherein said bacterium further comprises at least one polynucleotide whose expression is attenuated (compared to an unmodified starting strain) selected from the group consisting of:
the pck polynucleotide which codes for phosphoenol pyruvate carboxykinase,
the pgi polynucleotide which codes for glucose 6-phosphate isomerase, and
the poxB polynucleotide which codes for pyruvate oxidase.

19. The process of claim 9, which is a batch process.

20. The process of claim 9, which is a fed batch or repeated fed batch process.

21. The process of claim 9, which is a continuous process.

22. The process of claim 9, wherein said bacterium has been modified to express a decreased amount of malate dehydrogenase.

23. The bacterium of claim 22, wherein said malate dehydrogenase has the N-terminal amino acid residues of SEQ ID NO: 1.

24. The bacterium of claim 23, wherein said malate dehydrogenase comprises the amino acid sequence of SEQ ID NO: 3.

25. The bacterium of claim 24, wherein said malate dehydrogenase is encoded by a polynucleotide comprising nucleotides 536 to 1519 of SEQ ID NO: 2.

26. The bacterium of claim 25, wherein said polynucleotide comprises SEQ ID NO: 2.

* * * * *

SEQUENCE LISTING

```
<160> NUMBER OF SEQ ID NOS: 5

<210> SEQ ID NO 1
<211> LENGTH: 18
<212> TYPE: PRT
<213> ORGANISM: Corynebacterium glutamicum

<400> SEQUENCE: 1

Asn Ser Pro Gln Asn Val Ser Thr Lys Lys Val Thr Val Thr Gly Ala
1               5                   10                  15

Gly Gln

<210> SEQ ID NO 2
<211> LENGTH: 2663
<212> TYPE: DNA
<213> ORGANISM: Corynebacterium glutamicum
<220> FEATURE:
<221> NAME/KEY: CDS
<222> LOCATION: (536)..(1519)
<223> OTHER INFORMATION:

<400> SEQUENCE: 2
aaggcctttc ttatcgccaa agtgatagtg gatcatgcgc ttggacatgc cagatgcctt      60
cgcgattttc tccaatttgg tttcgctaaa accatcctct gcaaaaaatg tcagagcggt     120
ggctactacc tcttcagggg ttgcggtgtg tcctgaatca gattcaatga attcgctacc     180
ggcctggtct atgttttcgg catctcgacg tgatgtcgcc ataatcgatc aattcctttc     240
gggtaacgag aaaacgtgaa ttagaaacgg ggttaaggta aatatcaaag ataacaccat     300
cggcaaatcc cagctgacaa ctataaatgg tgcccgatat caggaaaaat tgcttgcaca     360
cgcgcgccga ttccccatga tgccctaaca tcttgcaggt gagggtaca tattggggca     420 attcggggt aattttgcag tatcgtcaag atcacccaaa actggtggct gttctctttt     480
aagcgggata gcatggggttc ttagaggacc ccctacaagg attgaggatt gttta atg    538
                                                                Met
                                                                  1 aat tcc ccg cag aac gtc tcc acc aag aag gtc acc gtc acc ggc gca    586
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Asn | Ser | Pro | Gln | Asn | Val | Ser | Thr | Lys | Lys | Val | Thr | Val | Thr | Gly | Ala |      |
|     |     |     |   5 |     |     |     |     |  10 |     |     |     |     |  15 |     |     |      |
| gct | ggt | caa | atc | tct | tat | tca | ctg | ttg | tgg | cgc | atc | gcc | aac | ggt | gaa |  634 |
| Ala | Gly | Gln | Ile | Ser | Tyr | Ser | Leu | Leu | Trp | Arg | Ile | Ala | Asn | Gly | Glu |      |
|     |     |  20 |     |     |     |     |  25 |     |     |     |     |  30 |     |     |     |      |
| gta | ttc | ggc | acc | gac | acc | cct | gta | gaa | ctg | aaa | ctt | ctg | gag | atc | cct |  682 |
| Val | Phe | Gly | Thr | Asp | Thr | Pro | Val | Glu | Leu | Lys | Leu | Leu | Glu | Ile | Pro |      |
|  35 |     |     |     |     |  40 |     |     |     |     |  45 |     |     |     |     |     |      |
| cag | gct | ctt | ggc | ggg | gca | gag | ggt | gtg | gct | atg | gaa | ctt | ctg | gat | tct |  730 |
| Gln | Ala | Leu | Gly | Gly | Ala | Glu | Gly | Val | Ala | Met | Glu | Leu | Leu | Asp | Ser |      |
|  50 |     |     |     |     |  55 |     |     |     |     |  60 |     |     |     |     |  65 |      |
| gcc | ttc | ccc | ctc | ctg | cga | aac | atc | acc | atc | acc | gcg | gat | gcc | aat | gag |  778 |
| Ala | Phe | Pro | Leu | Leu | Arg | Asn | Ile | Thr | Ile | Thr | Ala | Asp | Ala | Asn | Glu |      |
|     |     |     |     |  70 |     |     |     |     |  75 |     |     |     |     |  80 |     |      |
| gca | ttc | gac | ggc | gct | aat | gcg | gcg | ttt | ttg | gtc | ggt | gcg | aag | cct | cgc |  826 |
| Ala | Phe | Asp | Gly | Ala | Asn | Ala | Ala | Phe | Leu | Val | Gly | Ala | Lys | Pro | Arg |      |
|     |     |     |  85 |     |     |     |     |  90 |     |     |     |     |  95 |     |     |      |
| gga | aaa | ggc | gaa | gag | cgc | gca | gat | ttg | ctg | gct | aac | aac | ggc | aag | att |  874 |
| Gly | Lys | Gly | Glu | Glu | Arg | Ala | Asp | Leu | Leu | Ala | Asn | Asn | Gly | Lys | Ile |      |
|     |     | 100 |     |     |     |     | 105 |     |     |     |     | 110 |     |     |     |      |
| ttc | gga | cct | caa | ggt | aaa | gct | atc | aat | gac | aac | gcc | gca | gat | gac | att |  922 |
| Phe | Gly | Pro | Gln | Gly | Lys | Ala | Ile | Asn | Asp | Asn | Ala | Ala | Asp | Asp | Ile |      |
| 115 |     |     |     |     | 120 |     |     |     |     | 125 |     |     |     |     |     |      |
| cgt | gtc | cta | gtt | gtt | gga | aac | cca | gcg | aac | acc | aac | gcg | ttg | att | gct |  970 |
| Arg | Val | Leu | Val | Val | Gly | Asn | Pro | Ala | Asn | Thr | Asn | Ala | Leu | Ile | Ala |      |
| 130 |     |     |     |     | 135 |     |     |     |     | 140 |     |     |     |     | 145 |      |
| tca | gct | gcg | gcc | cca | gat | gtt | cca | gca | tcc | cgc | ttc | aac | gca | atg | atg | 1018 |
| Ser | Ala | Ala | Ala | Pro | Asp | Val | Pro | Ala | Ser | Arg | Phe | Asn | Ala | Met | Met |      |
|     |     |     |     | 150 |     |     |     |     | 155 |     |     |     |     | 160 |     |      |
| cgc | ctt | gat | cac | aac | cgt | gcg | atc | tcc | cag | ctg | gcc | acc | aag | ctt | ggc | 1066 |
| Arg | Leu | Asp | His | Asn | Arg | Ala | Ile | Ser | Gln | Leu | Ala | Thr | Lys | Leu | Gly |      |
|     |     |     | 165 |     |     |     |     | 170 |     |     |     |     | 175 |     |     |      |
| cgt | gga | tct | gcg | gaa | ttt | aac | aac | att | gtg | gtc | tgg | gga | aat | cac | tcc | 1114 |
| Arg | Gly | Ser | Ala | Glu | Phe | Asn | Asn | Ile | Val | Val | Trp | Gly | Asn | His | Ser |      |
|     |     | 180 |     |     |     |     | 185 |     |     |     |     | 190 |     |     |     |      |
| gca | acc | cag | ttc | cca | gac | atc | acc | tac | gca | acc | gtt | ggt | gga | gaa | aag | 1162 |
| Ala | Thr | Gln | Phe | Pro | Asp | Ile | Thr | Tyr | Ala | Thr | Val | Gly | Gly | Glu | Lys |      |
| 195 |     |     |     |     | 200 |     |     |     |     | 205 |     |     |     |     |     |      |
| gtc | act | gac | ctg | gtt | gat | cac | gat | tgg | tat | gtg | gag | gag | ttc | att | cct | 1210 |
| Val | Thr | Asp | Leu | Val | Asp | His | Asp | Trp | Tyr | Val | Glu | Glu | Phe | Ile | Pro |      |
| 210 |     |     |     |     | 215 |     |     |     |     | 220 |     |     |     |     | 225 |      |
| cgc | gtg | gct | aac | cgt | ggc | gct | gaa | atc | att | gag | gtc | cgt | gga | aag | tct | 1258 |
| Arg | Val | Ala | Asn | Arg | Gly | Ala | Glu | Ile | Ile | Glu | Val | Arg | Gly | Lys | Ser |      |
|     |     |     | 230 |     |     |     |     | 235 |     |     |     |     | 240 |     |     |      |
| tct | gca | gct | tct | gca | gca | tcc | tct | gcg | att | gat | cac | atg | cgc | gat | tgg | 1306 |
| Ser | Ala | Ala | Ser | Ala | Ala | Ser | Ser | Ala | Ile | Asp | His | Met | Arg | Asp | Trp |      |
|     |     |     | 245 |     |     |     |     | 250 |     |     |     |     | 255 |     |     |      |
| gta | cag | ggc | acc | gag | gcg | tgg | tcc | tct | gcg | gca | att | cct | tcc | acc | ggt | 1354 |
| Val | Gln | Gly | Thr | Glu | Ala | Trp | Ser | Ser | Ala | Ala | Ile | Pro | Ser | Thr | Gly |      |
|     |     | 260 |     |     |     |     | 265 |     |     |     |     | 270 |     |     |     |      |
| gca | tac | ggc | att | cct | gag | ggc | att | ttt | gtc | ggt | ctg | cca | acc | gta | tcc | 1402 |
| Ala | Tyr | Gly | Ile | Pro | Glu | Gly | Ile | Phe | Val | Gly | Leu | Pro | Thr | Val | Ser |      |
| 275 |     |     |     |     | 280 |     |     |     |     | 285 |     |     |     |     |     |      |
| cgc | aac | ggt | gag | tgg | gaa | atc | gtt | gaa | ggc | ctg | gag | att | tcc | gat | ttc | 1450 |
| Arg | Asn | Gly | Glu | Trp | Glu | Ile | Val | Glu | Gly | Leu | Glu | Ile | Ser | Asp | Phe |      |
| 290 |     |     |     |     | 295 |     |     |     |     | 300 |     |     |     |     | 305 |      |
| cag | cgc | gcc | cgc | atc | gac | gcg | aat | gct | cag | gaa | ttg | cag | gcc | gag | cgc | 1498 |
| Gln | Arg | Ala | Arg | Ile | Asp | Ala | Asn | Ala | Gln | Glu | Leu | Gln | Ala | Glu | Arg |      |
|     |     |     |     | 310 |     |     |     |     | 315 |     |     |     |     | 320 |     |      |

```
gag gca gtg cgc gac ttg ctc taatctttaa cgcatgactt cgcttttcga        1549
Glu Ala Val Arg Asp Leu Leu
              325 cgccccaacc ctccaacgcg tcaccgtttt cacgggctcg gcgctcggca gttcctcgct   1609 gtacacgcaa gcggctcaaa ccttggcgaa aaccgcggta gaccgcggca tcgacttggt   1669 ttacggtggc ggaaaagtgg ggctcatggg tatcgtcgcg gatgcgttcc tggaatcagg   1729 tggcgaagcc tttggcgtca tcacggaatc acttatgaag ggtgagcttg gcatgaaaa    1789 gctcaccgaa cttgaaatcg ttcctgatat gcacatccgc aagcgtcgca tggcagaact   1849 tggcgatggt tttatcgcca tgcccggtgg cgccggcacc ttggaagaac ttttcgaggt   1909 ctggacctgg caacagctgg gcattcatca aaagcccgtc gcactttatg atgtcgatgg   1969 tttttggcag cccctgctgg aaatgcttga gcagatgacc cagcgtggat ttatcaagcg   2029 agacttcttt gagtgcctca tcgtggaatc cgacccgcat gccctgctaa aggcaatgca   2089 gacctggact ccaccagcac caaaatggta actaaattgt gtgctcgacg gtaacgccgc   2149 cgagtatctt gatggaaatg gaagccacgc cgttgtcatt gactgtgatg gtttcttcta   2209 cttctgggcc atcgaaacgt gaaatctcgg tagcatccac atcggtgatg gagctatcaa   2269 aaggaatctt gatttcactg agcagggaaa tatctccggg gctgccatcc tcggacacgg   2329 tggagtattc cacgaacctg aaccaaccaa tgttgtgcac cgccttgtag catcgtttcg   2389 ccacggtcgc agaatcggtg tccggggcga tcagcgggtc aaagctcacg gcacgaccag   2449 aatcgtgctc acggaacaca ccgatgcctc gcgcaacgcg gtcccttagg tggaaaccag   2509 aggaagggtc agccgcgatg gccagaccca ccgcagtgga acctgagggg aatggggagc   2569 ggtggacacg gcggccgaaa cgctcgcgga gcaacctgga aacgagtggg agcgaggatc   2629 cactagttct agagcggccg ccaccgcggt ggag                              2663

<210> SEQ ID NO 3
<211> LENGTH: 328
<212> TYPE: PRT
<213> ORGANISM: Corynebacterium glutamicum

<400> SEQUENCE: 3

Met Asn Ser Pro Gln Asn Val Ser Thr Lys Lys Val Thr Val Thr Gly
1               5                   10                  15

Ala Ala Gly Gln Ile Ser Tyr Ser Leu Leu Trp Arg Ile Ala Asn Gly
                20                  25                  30

Glu Val Phe Gly Thr Asp Thr Pro Val Glu Leu Lys Leu Leu Glu Ile
            35                  40                  45

Pro Gln Ala Leu Gly Gly Ala Glu Gly Val Ala Met Glu Leu Leu Asp
        50                  55                  60

Ser Ala Phe Pro Leu Leu Arg Asn Ile Thr Ile Thr Ala Asp Ala Asn
65                  70                  75                  80

Glu Ala Phe Asp Gly Ala Asn Ala Ala Phe Leu Val Gly Ala Lys Pro
                85                  90                  95

Arg Gly Lys Gly Glu Glu Arg Ala Asp Leu Leu Ala Asn Asn Gly Lys
            100                 105                 110

Ile Phe Gly Pro Gln Gly Lys Ala Ile Asn Asp Asn Ala Ala Asp Asp
        115                 120                 125

Ile Arg Val Leu Val Val Gly Asn Pro Ala Asn Thr Asn Ala Leu Ile
    130                 135                 140

Ala Ser Ala Ala Ala Pro Asp Val Pro Ala Ser Arg Phe Asn Ala Met
145                 150                 155                 160
```

```
Met Arg Leu Asp His Asn Arg Ala Ile Ser Gln Leu Ala Thr Lys Leu
                165                 170                 175

Gly Arg Gly Ser Ala Glu Phe Asn Asn Ile Val Val Trp Gly Asn His
            180                 185                 190

Ser Ala Thr Gln Phe Pro Asp Ile Thr Tyr Ala Thr Val Gly Gly Glu
        195                 200                 205

Lys Val Thr Asp Leu Val Asp His Asp Trp Tyr Val Glu Glu Phe Ile
    210                 215                 220

Pro Arg Val Ala Asn Arg Gly Ala Glu Ile Ile Glu Val Arg Gly Lys
225                 230                 235                 240

Ser Ser Ala Ala Ser Ala Ala Ser Ser Ala Ile Asp His Met Arg Asp
                245                 250                 255

Trp Val Gln Gly Thr Glu Ala Trp Ser Ser Ala Ala Ile Pro Ser Thr
            260                 265                 270

Gly Ala Tyr Gly Ile Pro Glu Gly Ile Phe Val Gly Leu Pro Thr Val
        275                 280                 285

Ser Arg Asn Gly Glu Trp Glu Ile Val Glu Gly Leu Glu Ile Ser Asp
    290                 295                 300

Phe Gln Arg Ala Arg Ile Asp Ala Asn Ala Gln Glu Leu Gln Ala Glu
305                 310                 315                 320

Arg Glu Ala Val Arg Asp Leu Leu
                325

<210> SEQ ID NO 4
<211> LENGTH: 18
<212> TYPE: DNA
<213> ORGANISM: Artificial Sequence
<220> FEATURE:
<223> OTHER INFORMATION: synthetic DNA

<400> SEQUENCE: 4
aargtyacyg tyacyggy                                             18

<210> SEQ ID NO 5
<211> LENGTH: 17
<212> TYPE: DNA
<213> ORGANISM: Artificial Sequence
<220> FEATURE:
<223> OTHER INFORMATION: synthetic DNA

<400> SEQUENCE: 5
cgrttrtgrt cvarrcg                                              17
```